United States Patent [19]

Rehkopf et al.

[11] 4,369,785
[45] Jan. 25, 1983

[54] SURGICAL FLUID FLOW SYSTEM

[75] Inventors: Paul G. Rehkopf, Murrysville; Ronald Zdrojkowski, Pittsburgh, both of Pa.

[73] Assignee: Contemporary Ocu-Flo, Inc., Hollywood, Fla.

[21] Appl. No.: 123,487

[22] Filed: Feb. 21, 1980

[51] Int. Cl.³ .............................................. A61M 1/00
[52] U.S. Cl. .................................................. 128/276
[58] Field of Search .......................... 15/302, 321, 421; 128/276, 305; 137/205

[56] References Cited

U.S. PATENT DOCUMENTS 3,812,855  5/1974  Banko .................................. 128/276
4,168,707  9/1979  Douvas et al. ...................... 128/276
4,180,074  12/1979  Murry et al. ........................ 128/276

Primary Examiner—Robert W. Michell
Assistant Examiner—J. L. Kruter
Attorney, Agent, or Firm—Richard M. Saccocio

[57] ABSTRACT

Irrigation-aspiration fluid flow systems, including the electronic controls therefor, are disclosed for use with surgical removal of a cataracted lens of an eye of a human or animal. Irrigation flow is provided by gravitational forces and is primarily controlled thereby. Aspiration flow is accomplished by a vacuum pump in conjunction with high and low pressure relief valves. The system provides for purging of air from the irrigation and aspiration flow lines prior to surgery. Flashing pilot lights and on-off pilot lights indicate the readiness of the system for use during surgery and assures that the proper mode of operation will be achieved upon activation of a foot switch controlled by the operating surgeon.

10 Claims, 3 Drawing Figures

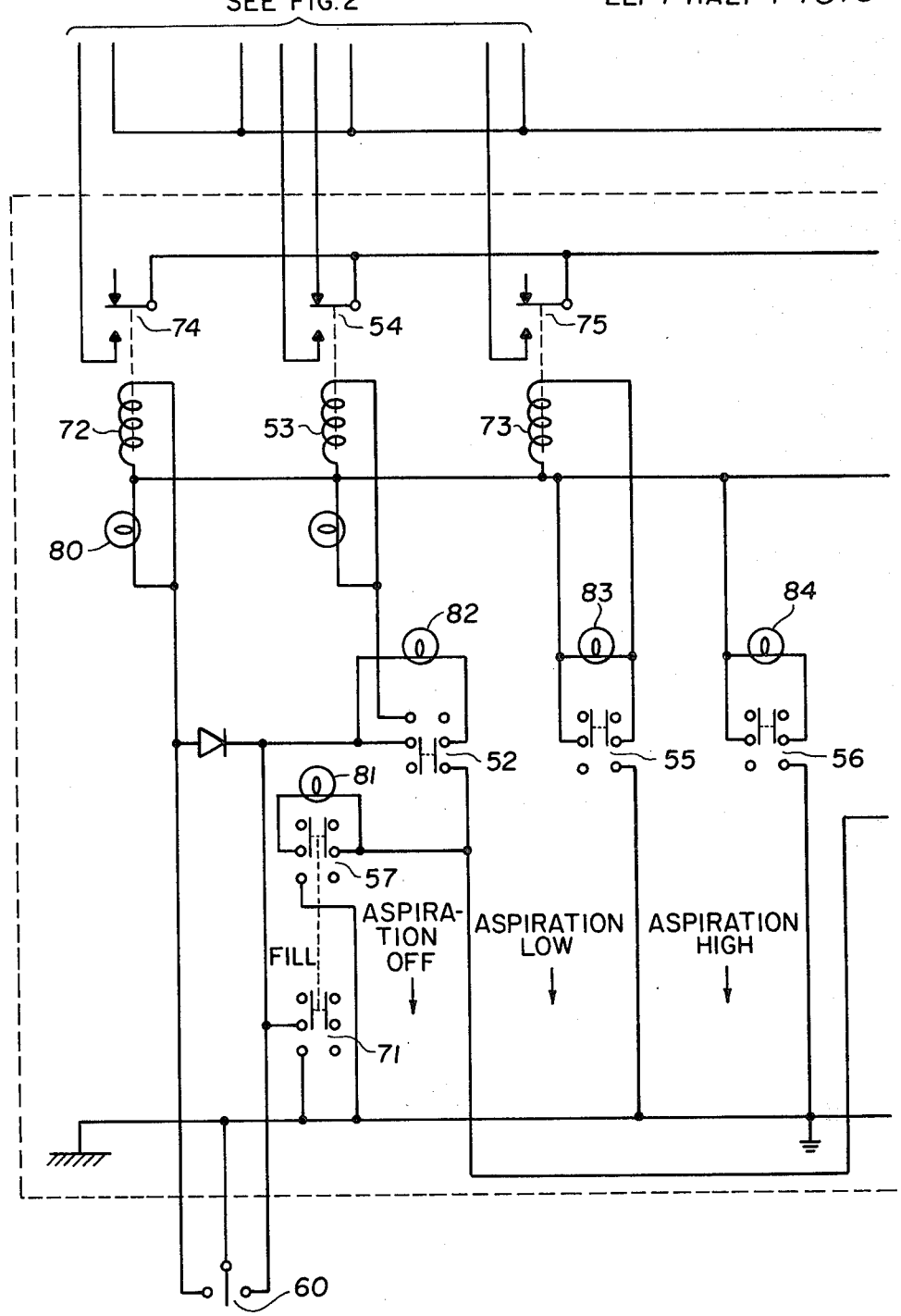

FIG. 3 RIGHT HALF
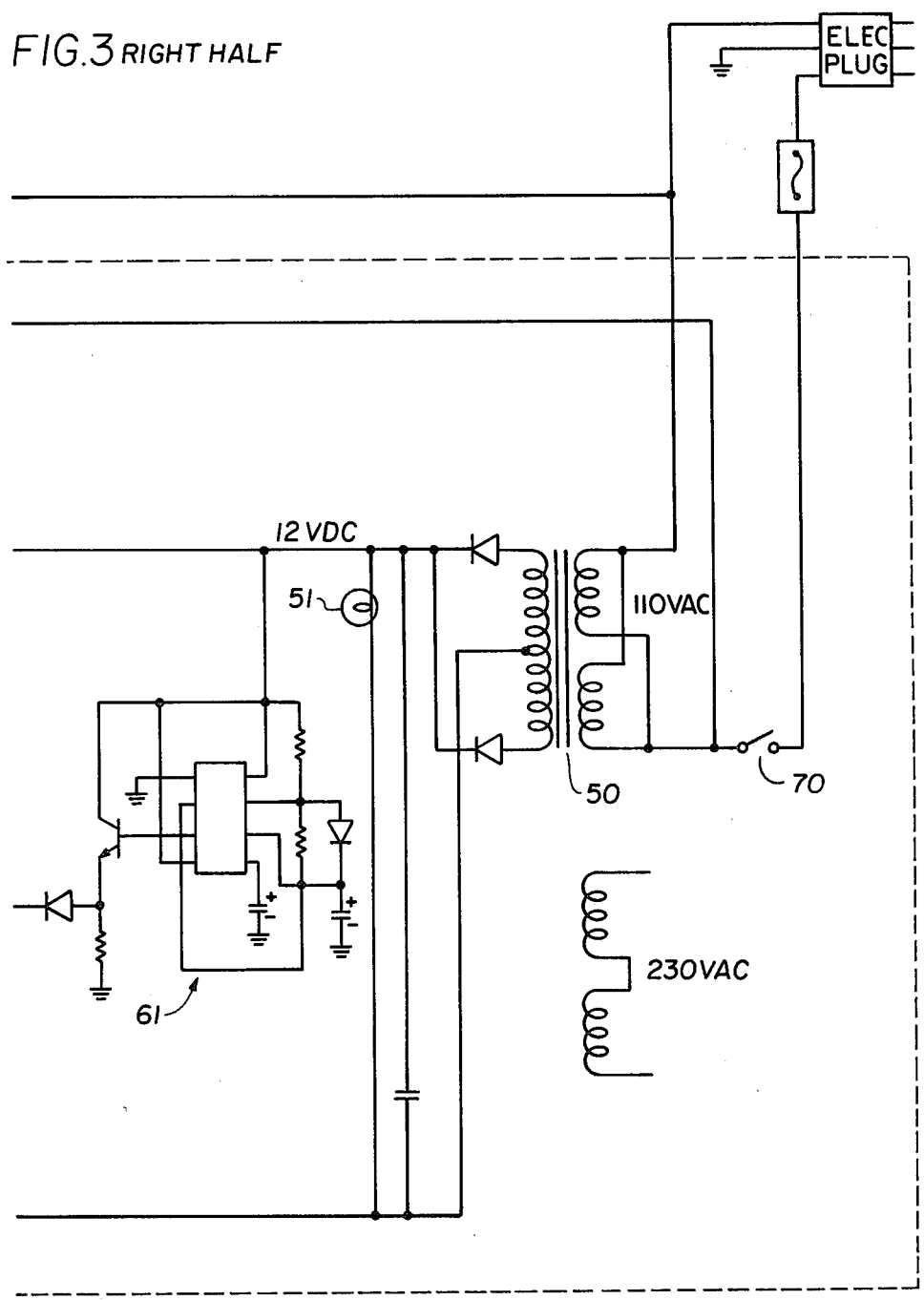

SURGICAL FLUID FLOW SYSTEM

BACKGROUND OF THE INVENTION

1. Field of the Invention

This invention relates, in general, to the field of ophthalmic surgical systems and in particular to a method and system for supplying and controlling irrigation fluid and suction pressure for aspiration flow to be supplied to a surgical instrument for extracapsular removal of a cataract from an eye.

2. Description of the Prior Art

In general, removal of a cataract from an eye involves either extracapsular or intracapsular techniques. Removal of the lens and its outer covering, the lens capsule, is known as intracapsular removal. Extracapsular removal of a cataract involves cutting away the anterior portion of the lens capsule which serves to expose the lens and then the cataract and the cortex may be removed.

The actual removal of the lens and the cortex is accomplished a number of ways. In U.S. Pat. No. 3,857,387 (1974), the inventor utilizes ultrasonic vibration to fragment hard cataracts and to gently wash out the fragments through a corneal incision in the eye, utilizing gravity-fed irrigation fluid flow. Thus, the irrigation fluid flow serves to keep the eye inflated and to remove the fragments. The object of this art being to eliminate the complexities (complex electronic and hydraulic equipment) introduced by aspiration of the emulsified lens while maintaining high surgical success rates.

In U.S. Pat. No. 3,732,858 (1973), by Anton Banko, apparatus is disclosed having a pair of movable jaws to sever material, such as portions of a lens, as the jaws are moved relative to each other. The severed material is then contained within a passage incorporated in the movable jaws and subsequently aspirated from the eye by suction forces. The disclosed movable jaws include a generally tubular outer member having a rotatable inner member which in combination define cutting edges. In operation, the lens is forced against the jaw portions which is then severed by the shearing action of the jaws and removed through the passageway which is vented to the atmosphere.

In another method, in U.S. Pat. No. 3,589,363 (1971), Anton Banko discloses apparatus for removing a cataract comprising a handpiece or instrument having an operative tip capable of vibrating at ultrasonic frequencies and having both a source of fluid and a pump whereby particles of the lens are severed utilizing ultrasonic vibrations and dispersed within the fluid and withdrawn from the operating site by the pump.

Wallach, in U.S. Pat. No. 4,024,866 (1977), discloses still another method, whereby a pulsating high velocity liquid jet is directed at an object such as a lens, disintegrating the same into small particles which are removed by sucking the fluid entraining the particles from the operating site.

In an even further method, the anterior capsule is cut by an appropriate instrument thereby exposing the lens. The nucleus of the lens, if any, is dislodged from the lens into the anterior chamber of the eye and is subsequently removed through an opening at the limbus. The remaining cortex of the lens is then sucked from the eye by a balanced combination of irrigation and aspiration flow through a double-barreled needle inserted into the eye at the incision at the limbus. The above-noted method and the apparatus associated therewith is more completely described in U.S. patent application filed 10/12/79, Ser. No. 6/84,180.

It cannot be stated with certainty as to which method or combination of methods of removing cataracts is in most widespread use today. In all probability, intracapsular removal of cataracts, whereby both the lens and the entire capsule covering the lens are removed as a unit, is the most prevalent. However, the use of ultrasonic vibrations (with either extracapsular surgery or intracapsular surgery) and the intracapsular method using suction to remove soft cataracts and cortex are extensively used. And, both of these methods are most often accompanied by the use of both irrigation flow and aspiration flow. The former flow generally being used to maintain the shape of the anterior chamber of the eye during the operation; while the latter flow is used to remove soft cataracts (for example, in children) and cortex as well as emulsified portions of hard cataracts. With these methods, therefore, it is necessary to have a first fluid flow system for purposes of irrigation and a second fluid flow system for asiration. In many systems, both the irrigation flow and aspiration flow are combined in one overall system.

As may well be expected, the fluid flow systems utilized with cataract surgery have undergone significant transformations. Indeed, in early cataract surgery (other than total removal of the lens and the capsule) many failures were attributable to the lack of adequate flow systems. It is now realized that it is imperative to maintain the shape of the eye and during the operation. Uncontrolled collapse of the shape of the eye almost always resulted in failure. Irrigation flow to the eye maintains the shape of the eye, but it must be properly controlled so as to prevent both underpressure and overpressure. Similarly, aspiration flow must be precisely controlled so as not to cause unwarranted evacuation of the fluid within an eye and so as not to cause an operating surgeon to remove portions of the eye not intended to be removed. Unfortunately, an operating surgeon's mechanical skill is not necessarily synonymous with his surgical skill. Fluid flow systems which require a high degree of mechanical skill are understandably highly undesirable. Even the best and most qualified surgeons cannot totally overcome deficiencies in mechanical equipment. Simplified, easily controllable, and reliable fluid flow systems are, therefore, a necessity in cataract surgery.

An example of a relatively early prior art fluid control system is disclosed in U.S. Pat. No. 3,589,363 (1971), by Anton Banko. In this teaching, the problem which still exists today, is succinctly stated to be that an equilibrium condition must exist at the operative site between the irrigation flow, the aspiration flow, and the leakage flow past the incisions. In a sense, this equilibrium condition is self-adjusting. For example, for a given aspiration flow rate, an increased irrigation flow rate will result in a higher leakage rate past the incision. While such a condition might be said to be "balanced", it is not desirable because of the high leakage rate past the incision. Thus, a properly balanced equilibrium condition is one whereby there is no overpressure or underpressure in the eye, there is not too high or too low of an aspiration flow rate, and there is not too high a flow rate past the incision. In attempting to achieve such a balanced equilibrium, the above, last-stated prior art disclosed separate irrigation and aspiration flow systems. The irrigation flow being variably controlled by a switch which regulates the pressure of the irrigation fluid supply. The aspiration flow being controlled by a vacuum pump and a number of solenoid valves which in combination provide an unspecified but constant suction force (with no flow at the operating tip) or an unspecified but constant pumping flow from the operating tip.

In 1974, in U.S. Pat. No. 3,812,855, Anton Banko disclosed a relatively sophisticated system for controlling pressurized irrigation fluid and suction pressure for aspiration flow for use with a single handpiece for removing cataracts. This system provides a great degree of versatility and adjustability in supplying a pressurized fluid (irrigation flow) with or without suction pressure—and, therefore, aspiration flow—being applied. The disclosed system also provides for reversing the flow to the handpiece to eject unwanted material which might clog the instrument. Since a positive pressure pump is utilized to pressurize the irrigation fluid, an adjustment by a hand valve allows for a change in the irrigation fluid flow rate. Similarly, the suction pressure for the aspiration flow is controllable but now by two valves. Also, a controller is used to prevent too high a suction pressure. In practice, it has been found, however, that such a system is too complicated and requires a high degree of mechanical ability to be properly operated.

In U.S. Pat. Nos. 4,019,514 (1977) and 3,920,014, Anton Banko again disclosed systems for controlling the infusion of fluid to and the evacuation of fluid and material from an operating field such as an eye. In these patents, the inventor recognizes the complexity of his prior teaching and attempts to simplify that system while maintaining the same operating or functioning modes. Again, sophisticated and versatile systems are attained; but still again, there is a great degree of complexity.

U.S. Pat. No. 3,857,387 (1974) discloses a method of removing cataracts using ultrasonic vibrations and gravity flow of irrigation fluid. Aspiration flow is not used. The inventor, in this teaching, relies on a flow past the incision—described as gentle lavage flow—to expel fragmented portions of the lens from the eye. Thus, he achieves a very simple system which involves only irrigation flow which is controlled by a hand-operated valve. While the simplicity of this system is intriguing, it is limited to cataract removal using ultrasonic vibrations and no aspiration flow. It would, therefore, not be applicable to the instant method of cataract removal which does utilize aspiration flow to remove the remaining cortex of hard cataracts.

Anton Banko, in U.S. Pat. No. 4,007,742 (1977) again addresses the problem of simplicity of operation and control in providing an irrigation and aspiration flow system. In this teaching, Banko employs gravitational forces to provide irrigation flow to the eye. The rate of flow being regulated by adjusting the height of a bottle containing the infusion fluid relative to the height of the operation field. In this system, a constant displacement pump of the peristaltic type is used to aspirate fragmented portions of the lens. Fragmentation being accomplished by the rotating action of a twist drill within a cylindrical housing an opening at the operative end and through which the twist drill extends. Variations in the flow resistance through the operative instrument due to the continuously changing effective viscosity of the effluent flow is accommodated by volumetric changes in the flexible exit flow lines (tubing shrinks) and the "vacuum" forces created by the constant displacement pump.

Considering the numerous attempts to provide fluid flow systems for use with cataract removal surgery, it is apparent that there still exists a need for a simplistic but effective system. Accordingly, it is an object of the present invention to provide an irrigation-aspiration fluid flow system for use with extracapsular extraction of cataracts which does not rely upon fragmentation or emulsification of the lens of the eye.

Another object of the present invention is to provide a simplified surgical fluid flow system which requires a minimum of mechanical ability to operate in an effective manner.

A further object of the invention is to provide an aspiration fluid flow system which is powered by a vacuum pump.

A still further object of the present invention is to provide an irrigation-aspiration fluid flow system for use with cataract surgery which is electronically operated and controllable by the operating surgeon during the surgery.

Another object of the invention is to provide a surgical fluid flow system which is capable of operating in separate irrigation, irrigation plus low aspiration, and irrigation plus high aspiration modes and which modes of operation are readily discernible to the operating surgeon.

Still additional objects and advantages of the present invention will become more apparent upon reference to the following specification and annexed drawings.

SUMMARY OF THE INVENTION

In accordance with the above objectives, the present invention is directed to a surgical fluid flow system providing irrigation and/or aspiration flow through a handpiece or operating instrument for extra-capsular removal of a cataracted lens and the remaining cortex of an eye. A gravity-fed irrigation flow subsystem is provided which includes a bottle containing appropriate irrigation fluid attached to an intravenous type of adjustable stand and an electrically operated valve to control the flow therefrom. In conjunction therewith, an aspiration fluid flow subsystem is provided, which subsystem is preset for high and low aspiration flow rates. A vacuum pump is employed with the aspiration subsystem to generate the aspiration flow from the eye whereby the remaining portions or cortex of a hard cataract are removed from an eye. In addition to the novel fluid flow subsystems provided herein, a novel electronic circuit is presented which serves to control the mode of operation and to provide a visual display so that the mode of operation is readily apparent to an operating surgeon. A foot switch, operable by the surgeon, is included within the control circuitry so as to achieve any desired mode of operation or a change in the mode of operation quickly, conveniently, and easily.

BRIEF DESCRIPTION OF THE DRAWINGS

For a more complete understanding of the invention, reference is had to the following description taken in conjunction with the accompanying drawings in which:

FIG. 3 is a schematic diagram of the irrigation-aspiration fluid flow system with particular emphasis on the electronic control function of the system.

DESCRIPTION OF THE PREFERRED EMBODIMENTS

Figure 1:
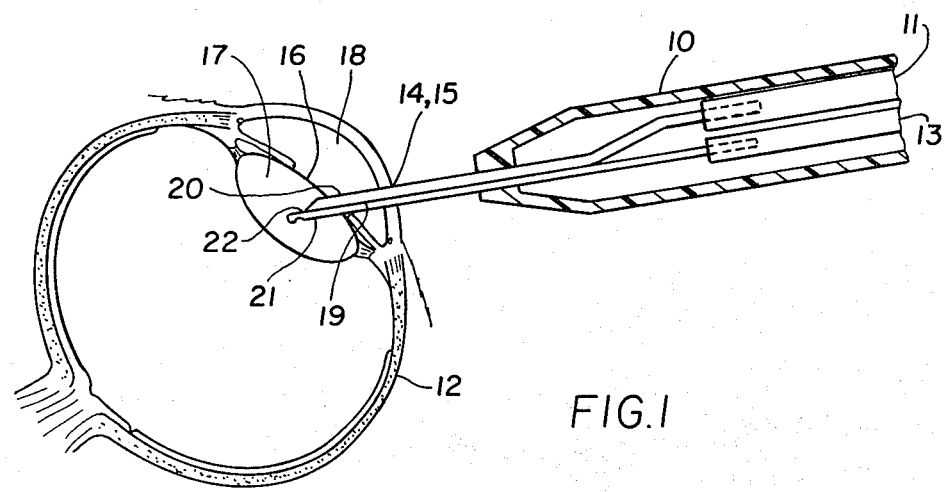
FIG. 1 is a plan view taken partially in cross section of an eye and a typical instrument for use with the fluid flow system of the present invention.

Referring now to the drawings, the system is described with respect to performing extracapsular, surgical removal of a cataract from an eye of either a person or an animal. However, it is to be noted that the below described system is not intended to be limited to the described operation. The system can be utilized in any type of operation utilizing irrigation flow in conjunction with aspiration flow removal or emulsified material, fragmented material, soft tissue or other objects, such as tumors.

FIG. 1 illustrates one type of surgical instrument or handpiece 10 which can be used with the fluid flow system of the instant invention. Handpiece 10 has a first line 11 for irrigation or influent liquid flow to the object of the surgery which in this case is eye 12. A second line 13 is used for aspiration or flow removal of the item intended to be removed from the eye 12. For purposes of this description, it is to be assumed that the operating surgeon has already made a small incision 14 in the limbus 15 and by using a cystotome, or bent disposable needle, has opened the anterior capsule 16 of the eye 12 exposing the lens 17. It is to be further assumed, in the case of a cataract having a hardened nucleus, that said nucleus has been prolapsed into the anterior chamber 18 and removed from the eye 12 through the incision 14 which has been sufficiently enlarged so that the nucleus can fit therethrough. The incision 14 was then reduced in size in preparation for aspirating the remaining portion of the lens 17 commonly known as the cortex. The double-barreled needle 19 was then inserted through incision 14 and positioned as shown within the lens proper of the eye 12. The influent or irrigation flow into the eye through line 11 exits handpiece 10 from portion 20 of needle 19. Irrigation flow is necessary to maintain the shape of the anterior chamber 18 throughout the operation. Should the eye 12 or the anterior chamber 18 collapse, there is the very real probability that the operation will be a failure. The remaining cortex is aspirated from the eye 12 through portion 21 of needle 19. The operative tip 22 of needle 19 has been developed over the years so as to preclude inadvertent aspiration of portions of an eye which are not intended to be removed.

From the above, it becomes readily apparent that a successful operation is directly dependent upon a number of factors. One factor, of course, is the skill and knowledge of the operating surgeon. While an extremely skillful surgeon can successfully perform an operation using the most primitive but adequate equipment, it is obviously beneficial to surgeons whose skill might be considered "normal" to be able to relay on equipment which is significantly superior to that classified as merely adequate. Given then, that some surgeons have normal skill, another factor is a proper operating instrument or handpiece such as that described above. A proper handpiece is one which among other things is, sterile, easily manipulated, gives the surgeon adequate vision, does not fatigue the surgeon, functions as designed or intended, and perhaps the most important, has the proper "feel" to allow the surgeon to apply his skills.

The proficiency of the team assisting the surgeon is still another factor. An additional factor is the adequacy of the facilities within which the operation is conducted. Notwithstanding that the listing of such factors has not been exhausted, still a further factor is the fluid flow system, including the control thereof, which is coupled to an operating instrument such as that above designated by numeral 10.

A proper fluid flow system is one which generates a balance between the influent or irrigation flow and the leakage flow past the incision plus the aspiration flow needed to remove the material such as the cortex from the eye. While such a statement appears to be a reiteration of the simple principle that input equals output, it is, in fact, more than it appears. For example, when a relatively solid portion of the lens is being aspirated, it will tend to clog the aspiration port of tip 22. At this point in time, the irrigation flow is continuing, and, therefore, to maintain flow balance, the leakage flow past the incision must increase. This increased flow could not only cause damage to a sensitive portion of the eye, but could as well cause damage by overpressurizing the anterior chamber 18. This potential problem must, therefore, be anticipated and overcome by the fluid flow system.

Similarly, a properly balanced system will not aspirate or remove fluid at a rate which is so high that the irrigation flow rate cannot maintain the shape of the eye.

Figure 2:
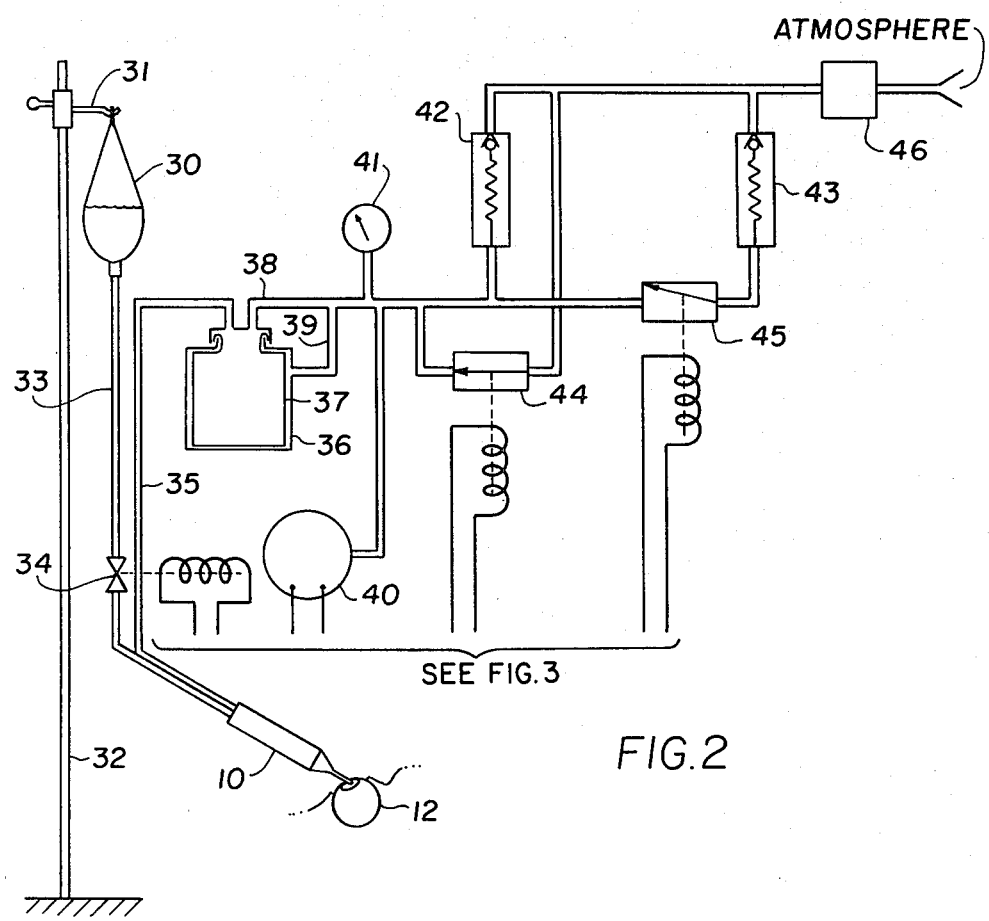
FIG. 2 is a pneumatic line diagram illustrating the various components of the irrigation-aspiration fluid flow system and their operation.

As shown in FIG. 2, irrigation flow is provided by a reservoir 30, containing an appropriate saline solution, which is suspended from arm 31. The height of arm 31 is adjustable on stand 32. Line 33 connects reservoir 30 to handpiece 10. The rate of flow of irrigation fluid is controlled by adjusting the height of arm 31 on stand 32. It will, therefore, be appreciated that the flow rate of an appropriate irrigation fluid is controlled by gravity. In practice, this relatively simple approach has been shown to be most effective. A high irrigation flow rate is not required, and as previously stated, could cause damage by overpressurizing the eye. In the system provided herein, there is no preset height position of reservoir 30. The operating surgeon, or a member of his team, appropriately positions reservoir 30 to achieve a desired flow rate prior to inserting tip 22 into the eye 11. By observing the shape of the eye 11 and the leakage flow past the incision 14 during the operation, the surgeon makes any necessary height adjustment. Irrigation flow, to the extent that it is turned on or off, is further controlled through the use of pinch valve 34. Pinch valve 34 is electronically activated by a foot switch controlled by the operating surgeon and functions by simply pinching line 33 between a pair of jaws, one of which is movable.

Still referring to FIG. 2, line 35 connects the aspiration channel of handpiece 10 to vacuum bottle 36. For convenience, vacuum bottle 36 contains a disposable liner 37 for collecting the effluent aspiration flow. Thus, liner 37 of bottle 36 is disposed of following an operation. Line 38 connects the interior of liner 37 to vacuum pump 40, while line 39 connects the exterior of liner 37 to vacuum pump 40. The vacuum on the external surface of liner 37 serves to prevent the liner from collapsing during use. An appropriate vacuum gauge 41, having a range between, for example, 0 to 30 inches of mercury, is connected to line 38. Gauge 41 provides a ready reference to the operating vacuum during the surgery. No other gauges are required.

A pair of preset relief valves 42 and 43 are connected in parallel to line 38. Relief valve 43 is set to achieve a low vacuum in the range of 4 to 6 inches of mercury; valve 42 is set to achieve a high vacuum in the range of 10 to 14 inches of mercury. Bypass valve 45 (normally open) operates in conjunction with the preset vacuum relief valves 42 and 43. When valve 45 is open, low vacuum is achieved; when valve 45 is closed (as shown), high vacuum is achieved. Valve 44 (normally open) serves to vent the vacuum to the atmosphere as when the aspiration flow system is off. Both valve 42 and valve 43 are electronically controlled solenoid valves. Filter 46, which vents to the atmosphere, is connected to line 38 in the manner illustrated in the drawing so as to be effective whether high or low vacuum is being utilized. It is preferred that vacuum lines 38 and 39 and all the connections therewith, the various components in the aspiration flow system of FIG. 2, be permanently bonded and made of rigid tubing so as to prevent either leakage or kinking and collapsing during use. Line 35 may be fabricated from nonrigid plastic tubing, such as Tygon, which has a sufficiently thick wall to prevent kinking. Bottle 36 is of sufficiently large volume, such as 1600 cc, so that any temporary clogging of handpiece 10 during aspiration is accommodated by bottle 36. The large volume of bottle 36 thereby prevents high vacuum pressures during aspiration even when channel 21 of needle 19 is temporarily clogged by a relatively large piece of cortex. In this manner, bottle 36 acts as a vacuum damper to prevent abrupt differential vacuum pressures from adversely affecting the surgery.

The electronic control circuitry for the irrigation-aspiration flow system is shown in FIG. 3. FIG. 2 and FIG. 3 are to be taken together in the following description.

Either 110 VAC or 220 VAC is input to the control circuitry and converted to 12 VDC, nominal by an appropriate transformer 50 in conjunction with a rectifier. A pilot light 51 is provided so that it may be readily ascertained that electric power is being supplied. Switch 52 turns the aspiration system on and off. In the position shown, switch 52 is off and no voltage is being supplied to coil 53 which in turn maintains switch 54 in an open position. When switch 54 is open, no current flows through the coil of solenoid valve 44 which maintains its normally open position and vents the vacuum flow lines 38 and 39 to the atmosphere.

When switch 52 is moved to the on position, valve 44 is caused to close which brings into service either the high 42 or the low 43 vacuum relief valves. Switch 55 allows for a low level of aspiration; switch 56 allows for high level of aspiration. Before either a low or a high level of aspiration flow is effectuated, switch 52 must, of course, be activated to an on position.

Foot switch 60 provides for: irrigate off; only irrigate on; irrigate and aspirate (either high or low) on modes of operation.

Fill switch 57 bypasses foot switch 60 in allowing the aspiration flow system and the irrigation flow system to be activated independently of foot switch 60. Fill switch 57 allows a nurse or technician to fill both aspiration flow line 35 and irrigation flow line 33 prior to actual use during an operation so that activation of foot switch 60 by an operating surgeon immediately results in the desired mode of operation of the fluid systems.

The portion of the control circuit designated by the numeral 61 is a flasher circuit which allows the lights of switches 52 and 57 to flash so that the operating surgeon can readily distinguish whether the aspiration system is off or on, or if the fill switch is off or on mode.

The flow systems as provided herein will now be described in preparation of and during an operation involving extracapsular removal of a cataracted lens.

An operating instrument or handpiece 10 is connected to irrigation flow line 33 and aspiration flow line 35. The main power to the aspiration flow system is turned on by activating switch 70. Foot switch 60 is in the neutral or center position so that neither the irrigation nor the aspiration flow system is activated. Fill switch 57, aspiration switch 52, aspiration low switch 55 and aspiration high switch 56 are all off. Switch 71 is likewise off. Coils 72, 53, and 73 are not energized and, therefore, switches 74, 54 and 75, respectively, are off or open. In this manner, pinch valve 34 is closed so that there is no irrigation flow from reservoir 30 to handpiece 10. Valve 44 is open, venting vacuum flow lines 38 and 39 to the atmosphere through filter 46. Valve 45 being normally open, is also open, but is not in service due to valve 44 being open. The vacuum pump 40 is on.

A nurse or a technician inserts tip 19 of handpiece 10 into a suitable container (not shown) and activates switches 71 and 52. Activation of switch 71 causes pinch valve 34 to open. Irrigation fluid then flows from reservoir 30 through line 33 to handpiece 10 and out of port 20 of needle 19. Irrigation flow then fills the container (not shown) within which the nurse or technician has inserted tip 19. The irrigation flow system has now been completely purged of air.

Since fill valve 52 was also activated when switch 71 was activated, current is supplied through switch 52 thereby energizing coil 53. Switch 54 is thereby closed, which then closes valve 44. The aspiration flow system is no longer vented to the atmosphere, and since only the vacuum pressure relief valve 42 is in service, (valve 45 is still closed) high aspiration flow results. The irrigation fluid filling the container (not shown) held by the nurse or technician and within which the needle 19 of handpiece 10 is inserted, is then sucked up through line 13 of handpiece 10, through line 35 and flows into bottle 36. In this manner, the aspiration flow lines are completely purged of air prior to the operation. Once purging is complete, the nurse or technician shuts off fill valve 52 and switch 71. Pinch valve 34 is thereby closd, maintaining the fluid within the irrigation flow lines.

Flasher network 61 and the various pilot lights are included to allow the surgeon or members of his operating team to visually and instantly ascertain the mode of operation of the fluid system at any given time. When foot switch 60 is positioned left of center or if fill switch 57 is activated, pilot light 80 is on indicating pinch valve 34 is open and irrigation fluid is flowing. When fill switch 57 is activated, pilot light 81 is flashing. When aspiration on-off switch 57 is off and foot switch 60 is positioned right of center, then irrigation flow is achieved but aspiration flow is off and pilot light 82 flashes. Flasher network 61, therefore, activates either pilot light 81 or pilot light 82.

When the nurse or technician activates fill switch 57 and aspiration on-off switch 52 to purge the irrigation and the aspiration flow systems, as previously stated, irrigation flow and high aspiration flow results; also, pilot light 81 flashes. Once purging is complete, the nurse shuts off fill switch 57 (pilot light 81 stops flashing) and should not shut off switch 52. If the nurse inadvertently shuts off switch 52, the operating surgeon will get irrigation flow but not aspiration flow when he positions foot switch 60 right of center to the irrigation plus aspiration flow position. At this point, pilot light 82 begins flashing to alert the surgeon of this unwanted situation and corrective measures may be taken. If switch 52 is correctly left on after purging is complete, pilot light 82 will not flash when the surgeon activates foot switch 60.

Pilot lights 83 and 84 are on or off lights; hence, they are not included within the flasher network 61. They indicate whether low or high aspiration flow respectively is selected. It is to be noted that activation of switch 56 merely results in lighting of pilot light 84. In and of itself, switch 56 does not achieve high aspiration flow rates. Low or high aspiration flow is achieved during the operation by activation or deactivation of switch 55 in conjunction with foot switch 60.

Notwithstanding that the embodiments of the invention described above in detail in conjunction with the accompanying drawings are primarily intended for use with extracapsular surgical removal of cataracts from an eye of a human or an animal, it is to be understood that the invention is not to be limited to the described embodiments, and that various changes and modifications may be made without departing from the scope or spirit of the invention, and which modifications and changes are intended to form a part of the described and claimed invention.

We claim:

1. A fluid flow system adapted to be used with an ophthalmic instrument having an influent flow channel and an effluent flow channel comprising:

an influent flow subsystem including a fluid reservoir, means for adjusting the differential pressure between said fluid reservoir and said influent flow channel, and means for controlling the flow of fluid from said fluid reservoir to said influent flow channel;

an effluent flow subsystem including means for applying a vacuum at said effluent flow channel, means for controlling the vacuum pressure at said effluent flow channel, and container means for collecting the effluent flow from said effluent flow channel, comprising a bottle having a cap thereon and a liner inserted therein, said liner being sealingly connected between said bottle and said cap, the interior of said liner and container being flow connected to said effluent flow channel of said instrument, and whereby the interior and exterior of said liner are flow connected to said vacuum means, said fluid flow system further comprising means for selecting a first mode of operation comprising influent flow to said instrument, or a second mode of operation comprising influent flow to and effluent flow from said instrument, and means for purging air from between said fluid reservoir and said influent flow channel and for purging air from between said effluent flow channel and said effluent flow container means prior to using said instrument during surgery.

2. The system of claim 1, wherein said bottle and liner include means for absorbing fluxuations in suction pressure caused by a temporary clogging of said effluent flow channel of said instrument.

3. The system of claim 2, wherein said means for absorbing suction pressure fluxuations comprises the volumetric capacity of said bottle and said liner.

4. The system of claim 3, wherein said bottle and said liner have a volumetric capacity of approximately 1600 cc.

5. A fluid flow system adapted to be used with an ophthalmic instrument having an influent flow channel and an effluent flow channel comprising:

an influent flow subsystem including a fluid reservoir, means for adjusting the differential pressure between said fluid reservoir and said influent flow channel, and means for controlling the flow of fluid from said fluid flow reservoir to said influent flow channel; and an effluent flow subsystem including means for applying a vacuum within said effluent flow channel, and means for achieving at least two different suction pressures within said effluent flow channel comprising a first pressure relief valve set to achieve a high vacuum pressure, and a second pressure relief valve set to achieve a low vacuum pressure, said first and second relief valves being vented to the atmosphere and flow connected in parallel with each other, with one of said relief valves having a shutoff valve in series connection therewith such that one or the other said relief valves is in operation at a given time, and a bypass valve for bypassing said first and second relief valves and venting said effluent flow subsystem to the atmosphere; and container means for collecting the effluent flow from said effluent flow channel; and said fluid flow system further comprising means for selecting a first mode of operation comprising influent flow to said instrument, and a second mode of operation comprising influent flow to and effluent flow from said instrument; and, means for purging air from between said fluid reservoir and said influent flow channel and for purging air from between said effluent flow channel and said effluent flow container means prior to using said instrument during surgery.

6. The system of claim 5, wherein said bypass valve is arranged in parallel with said parallel connected pressure relief valves.

7. A fluid flow system adapted to be used with an ophthalmic instrument having an influent flow channel and an effluent flow channel comprising:

an influent flow subsystem including a fluid reservoir, means for adjusting the differential pressure between said fluid reservoir and said influent flow channel, and means for controlling the flow of fluid from said fluid reservoir to said influent flow channel; and an effluent flow subsystem including means for applying a vacuum within said fluid flow channel, means for controlling the vacuum pressure within said effluent flow channel including an effluent high or effluent low switch and means for achieving at least two different suction pressures within said effluent flow channel comprising a first pressure relief valve set to achieve a high vacuum pressure, and a second pressure relief valve set to achieve a low vacuum pressure, said first and second relief valves being vented to the atmosphere and flow connected in parallel with each other, with one of said relief valves having a shutoff valve in series connection therewith such that one or the other of said relief valves is in operation at a given time, and a bypass valve for bypassing said first and second relief valves and venting said effluent flow subsystem to the atmosphere, and container means for collecting the effluent flow from said effluent flow channel; and said fluid flow system further comprising means for selecting a first mode of operation comprising influent flow to said instrument and a second mode of operation comprising influent flow to and effluent flow from said instrument, said effluent high or low switch being electronically connected to said mode operating switch; and, means for purging air from between said fluid reservoir and said influent flow channel and for purging air from between said effluent flow channel and said effluent container means prior to using said instrument.

8. The system of claim 7, including effluent on-off switch means for activating said effluent flow subsystem, and for overriding said mode selecting switch.

9. The system of claim 8, wherein said separate air purging means comprises an electronic fill switch electrically connected to override said mode selecting switch and upon activation causes said influent flow subsystem to operate and said effluent high subsystem to operate.

10. The system of claim 9, including flasher means, and pilot lights connected to each of said effluent on-off switch, said fill switch, said influent subsystem flow control means, said effluent high switch and said effluent low switch, said flasher means for flashing of said fill switch pilot light when said fill switch is activated and for flashing said effluent on-off pilot light when said on-off switch is off and said mode selecting switch is set for influent and effluent flow.

* * * * *